United States Patent
Mougeot et al.

(10) Patent No.: US 10,400,271 B1
(45) Date of Patent: Sep. 3, 2019

(54) COMPOSITIONS AND METHODS FOR GENETIC MARKERS TO IDENTIFY RISK OF ORAL MUCOSITIS

(71) Applicant: The Charlotte-Mecklenburg Hospital Authority, Charlotte, NC (US)

(72) Inventors: Jean-Luc C. Mougeot, Charlotte, NC (US); Farah K. B. Mougeot, Charlotte, NC (US)

(73) Assignee: The Charlotte-Mecklenburg Hospital Authority, Charlotte, NC (US)

( * ) Notice: Subject to any disclaimer, the term of this patent is extended or adjusted under 35 U.S.C. 154(b) by 0 days.

(21) Appl. No.: 16/285,819

(22) Filed: Feb. 26, 2019

Related U.S. Application Data

(60) Provisional application No. 62/635,235, filed on Feb. 26, 2018.

(51) Int. Cl.

| | | |
|---|---|---|
| *C07H 21/04* | (2006.01) | |
| *C12Q 1/68* | (2018.01) | |
| *C12Q 1/6827* | (2018.01) | |
| *C12Q 1/6858* | (2018.01) | |
| *C12Q 1/6876* | (2018.01) | |
| *G16H 50/30* | (2018.01) | |
| *G16H 50/20* | (2018.01) | |

(52) U.S. Cl.
CPC ......... *C12Q 1/6827* (2013.01); *C12Q 1/6858* (2013.01); *C12Q 1/6876* (2013.01); *G16H 50/20* (2018.01); *G16H 50/30* (2018.01); *C12Q 2600/118* (2013.01); *C12Q 2600/156* (2013.01); *C12Q 2600/158* (2013.01)

(58) Field of Classification Search
None
See application file for complete search history.

(56) References Cited

PUBLICATIONS

Sonis et al. (Oral Diseases, vol. 19, pp. 721-727, 2013) (Year: 2013).*
Bahrani-Mougeot et al. "Molecular Analysis of oral and Respiratory Bacterial Species Associated with Ventilator-Associated Pneumonia" Journal of Clinical Microbiology, 45(5):1588-1593 (2007).
Bowen et al. "Advances in the understanding and management of mucositis during stem cell transplantation" Current Opinion in Supportive and Palliative Care, 11(4):341-346 (2017) (Abstract only).
Chaveli-Lopez et al. "Treatment of oral mucositis due to chemotherapy" Journal of Clinical and Experimental Dentistry, 8(2):e201-e209 (2016).
Kirk et al. "Text mining-based in silico drug discovery in oral mucositis caused by high-dose cancer therapy" Supportive Care in Cancer, 26(8):2695-2705 (2018).
Mougeot et al. "Microarray analyses of oral punch biopsies from acute myeloid leukemia (AML) patients treated with chemotherapy" Oral Surgery, Oral Medicine, Oral Pathology and Oral Radiology, 112(4):446-452 (2011) (Abstract only).
Mougeot et al. "Use of archived biopsy specimens to study gene expression in oral mucosa from chemotherapy-treated cancer patients" Oral Surgery, Oral Medicine, Oral Pathology and Oral Radiology, 115(5):630-637 (2013) (Abstract only).
Mougeot et al. "Associations between bacteremia from oral sources and distant-site infections: tooth brushing versus single tooth extraction" Oral Surgery, Oral Medicine, Oral Pathology and Oral Radiology, 119(4):430-435 (2015) (Abstract only).
Mougeot et al. "Concordance of HOMIM and HOMINGS technologies in the microbiome analysis of clinical samples" Journal of Oral Microbiology, 8(30379):1-9 (2016).
Mougeot et al. "Porphyromonas gingivalis is the most abundant species detected in coronary and femoral arteries" Journal of Oral Microbiology, 9(1):1281562 (2017).
Mougeot et al. "Conditioning Therapy-Induced Oral Mucositis-Associated Single Nucleotide Polymorphisms (SNPs) Identified by Exome Sequencing Analysis: A Pilot Study" Abstract for Annual Meeting of the Multinational Association of Supportive Care in Cancer (MASCC) (1 page) (Jun. 25-28, 2018).
Mougeot et al. "Conditioning Therapy-Induced Oral Mucositis-Associated Single Nucleotide Polymorphisms (SNPs) Identified by Exome Sequencing Analysis: A Pilot Study" Support Care Cancer, Annual Meeting on Supportive Care in Cancer, 26(Suppl 2):S148-S149 (eP191) (2018).
Mougeot et al. "Validation of a Panel of Single Nucleotide Polymorphisms (SNPs) Candidates Associated with Oral Mucositis in Patients Undergoing Conditioning Therapy for Hematopoietic Stem Cell Transplant (HSCT)" Abstract, 1 page (2018).
Mougeot et al. "Caries-associated oral microbiome in head and neck cancer radiation patients: a longitudinal study" Journal of Oral Microbiology, 11(1):1586421 (2019).
Napenas et al. "Molecular methodology to assess the impact of cancer chemotherapy on the oral bacterial flora: a pilot study" Oral Surgery, Oral Medicine, Oral Pathology and Oral Radiology, 109(4):554-560 (2010) (Abstract only).
Shah et al. "Expression of ETS1 and LEF1 in salivary glands of Sjögren syndrome patients" Oral Diseases, 25:164-173 (2019).
Xu et al. "Detecting very low allele fraction variants using targeted DNA sequencing and a novel molecular barcode-aware variant caller" BMC Genomics, 18(5):1-11 (2017).

* cited by examiner

*Primary Examiner* — Jeanine A Goldberg
(74) *Attorney, Agent, or Firm* — Myers Bigel, P.A.

(57) ABSTRACT

The present invention provides methods and compositions involving genetic markers and their association with oral mucositis occurring in patients who are treated with cancer therapy and/or conditioning therapy for hematopoietic stem cell transplantation.

3 Claims, No Drawings
Specification includes a Sequence Listing.

COMPOSITIONS AND METHODS FOR GENETIC MARKERS TO IDENTIFY RISK OF ORAL MUCOSITIS

STATEMENT OF PRIORITY

This application claims the benefit, under 35 U.S.C. § 119(e), of U.S. Provisional Application No. 62/635,235, filed Feb. 26, 2018, the entire contents of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 1184-31_ST25.txt, 1,312 bytes in size, generated on Jul. 9, 2019 and filed via EFS-Web, is provided in lieu of a paper copy. This Sequence Listing is incorporated by reference into the specification for its disclosures.

FIELD OF THE INVENTION

The present invention relates to genetic polymorphisms signatures and their association with oral mucositis in patients with hematologic cancer receiving radiation and/or chemotherapy or patients receiving conditioning regimen in preparation for hematopoietic stem cell transplant (HSCT) (e.g., cancer patients, patients with immunodeficiency condition, patients with other blood-related disorder, or other condition requiring HSCT).

BACKGROUND OF THE INVENTION

Oral mucositis (OM) is a common dose-limiting side effect of conditioning therapy used in cancer or immunodeficiency treatment of hematopoietic stem cell transplant (HSCT) patients. There is a need to identify genetic markers predictive of risk and severity of OM following radiation and/or chemotherapy.

The present invention overcomes previous shortcomings in the art by providing methods and compositions employing genetic biomarkers for prediction of risk for oral mucositis associated with cancer therapy and conditioning for HSCT.

DETAILED DESCRIPTION OF THE INVENTION

For the purposes of promoting an understanding of the principles of the present invention, reference will now be made to particular embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the invention relates.

The present invention is based on the unexpected discovery that a subject's genetic markers can be used to predict the subject's risk of having or developing oral mucositis associated with radiation therapy and/or chemotherapy and/or conditioning therapy for HSCT. Accordingly, in one embodiment, the present invention provides a method of identifying a subject (e.g., a subject who has undergone and/or will undergo hematopoietic stem cell transplantation (HSCT) and/or a subject who has undergone and/or will undergo chemotherapy and/or radiation therapy) as having an increased risk of developing oral mucositis, comprising: a. obtaining a DNA sample from the subject; b. contacting the DNA sample from the subject with reagents to determine the presence or absence of the following risk alleles: 1. GG at single nucleotide polymorphism (SNP) site rs4847278; 2. GG at SNP site rs10797854 and GG at SNP site rs20560 and CC at SNP site rs944970 and CC at SNP site rs1062044 and AA at SNP site rs944971 and GG at SNP site rs6424888 and CC at SNP site rs20563 and CC at SNP site rs2333620 (combined SNP genotype); 3. AA at SNP site rs7373116; 4. GA at SNP site rs61742149; 5. AA at SNP site rs10935321; and 6. TT at SNP site rs111482845 and TT at SNP site rs11728441 (combined SNP genotype); and c. detecting one or more of: the single risk alleles of (1), (3), (4), or (5) or the multiple risk alleles of (2) or (6) in the DNA sample, thereby identifying the subject as having an increased risk of developing oral mucositis.

The method described above, can further comprise the steps of: d. contacting the DNA sample with reagents to determine the presence of absence of the following risk alleles: 7. GG at SNP site rs147960186; 8. GG at SNP site rs11787880; 9. AA at SNP site rs10973387; and 10. AA at SNP site rs4030473 and GG at SNP site rs5915052 (combined SNP genotype); and e. detecting one or more of the single risk alleles of (7), (8) or (9) or the multiple risk alleles of (10) in the DNA sample, thereby identifying the subject as having an increased risk of developing oral mucositis.

In some embodiments, the methods of this invention can further comprise administering to the subject a treatment to optimize wound healing, based on the initial knowledge of a risk genotype, a probiotic diet to reduce levels of proinflammatory hydrogen sulfide or methylmercaptan produced by oral bacteria, an oral hygiene protocol, amifostine, palifermin, benzidamine, calcium phosphate, cryotherapy, iseganan, a cryoprotective (e.g., sucralfate, oral glutamine, hyaluronic acid), a growth factor, topical polyvinylpyrrolidone, low power laser irradiation, gene therapy treatment (e.g., AG013, Oragenics), and any combination thereof.

In some embodiments, a wound healing treatment would be a mouth rinse-based gene therapy such as AG013 (*Lactococcus lactis* delivering human trefoil factor protein [hTFF1], which is not a growth factor. hTFF1 protects the mucosa from insults, stabilizes the mucus layer and affects healing of the epithelium. Proteins and/or nucleic acids (such as small inhibitory siRNAs) may be delivered as an oral rinse (e.g., to minimize systemic side effects).

The present invention further provides a method of guiding clinical decision making for a subject in need of radiation therapy and/or chemotherapy and/or in need of conditioning therapy for HSCT, comprising: a. obtaining a DNA sample from the subject; b. contacting the DNA sample from the subject with reagents to determine the presence or absence of the following risk alleles: 1. GG at single nucleotide polymorphism (SNP) site rs4847278; 2. GG at SNP site rs10797854 and GG at SNP site rs20560 and CC at SNP site rs944970 and CC at SNP site rs1062044 and AA at SNP site rs944971 and GG at SNP site rs6424888 and CC at SNP site rs20563 and CC at SNP site rs2333620 (combined SNP genotype); 3. AA at SNP site rs7373116; 4. GA at SNP site rs61742149; 5. AA at SNP site rs10935321; and 6. TT at SNP site rs111482845 and TT at SNP site rs11728441 (combined SNP genotype); c. detecting one or more of: the single risk alleles of (1), (3), (4), or (5) or the multiple risk alleles of (2) or (6) in the DNA sample, thereby identifying the subject as having an increased risk of developing oral mucositis; and d. administering a therapy to prevent, ameliorate and/or reduce the symptoms of oral mucositis to the subject before, during and/or after the radiation therapy and/or chemotherapy and/or conditioning therapy for HSCT.

In some embodiments of the method above, the therapy to prevent, ameliorate or reduce the symptoms of oral mucositis can be a treatment to optimize wound healing, a probiotic diet to reduce levels of proinflammatory hydrogen sulfide or methylmercaptan produced by oral bacteria, an oral hygiene protocol, amifostine, palifermin, benzidamine, calcium phosphate, cryotherapy, iseganan, a cryoprotective (e.g., sucralfate, oral glutamine, hyaluronic acid), a growth factor, topical polyvinylpyrrolidone, low power laser irradiation, and any combination thereof.

In further embodiments, the present invention provides a method of correlating a genetic marker profile of a subject with oral mucositis associated with radiation therapy and/or chemotherapy and/or conditioning therapy for HSCT, comprising: a) identifying a subject or population of subjects having oral mucositis associated with radiation and/or chemotherapy and/or conditioning therapy for HSCT; b) determining the genetic marker profile of the subject or of each of the subjects of the population of (a); and c) correlating the presence of the genetic marker profile of step (b) with oral mucositis in the subject or population of subjects.

The methods of this invention can be used to identify and/or monitor a subject for oral mucositis who may benefit from treatment, which can be prior to, during and/or following radiation therapy and/or chemotherapy and/or conditioning therapy for HSCT. The treatment of such subjects can also be monitored and/or modified according to the methods described herein.

It is understood that although the methods of this invention can be used in isolation, they can also form a part of a multimarker approach for diagnosing and/or identifying risk of oral mucositis associated with radiation therapy and/or chemotherapy and/or conditioning therapy for HSCT. Thus, the methods of the present invention might not only be used in place of a measurement of other biomarkers, but might also be used in combination, or in addition to the measurement or analysis of one or more other markers or biomarkers known to be associated with oral mucositis associated with radiation therapy and/or chemotherapy and/or conditioning therapy for HSCT.

Techniques that can be used to identify single nucleotide polymorphisms (SNPs) of this invention can include, but are not limited to, whole genome exome sequencing (using next generation sequencing technology, i.e., NGS), targeted allelic sequencing, which focuses on the target genes instead of the whole genome, by generating amplicons by PCR, and/or techniques based on Taqman Sanger sequencing, which is equivalent to the targeted allelic sequencing, but does not use NGS. All techniques are valid to determine the SNPs of this invention.

Definitions

The terms "a," "an" and "the" are used herein to refer to one or to more than one (i.e., at least one) of the grammatical object of the article. By way of example, "an element" means at least one element and can include more than one element (e.g., a multiplicity or plurality of elements).

As used herein, the term "and/or" refers to and encompasses any and all possible combinations of one or more of the associated listed items, as well as the lack of combinations when interpreted in the alternative ("or").

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

As used herein, "one or more" can mean one, two, three, four, five, six, seven, eight, nine, ten or more, up to any number.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, *In re Herz,* 537 F.2d 549, 551-52, 190 USPQ 461, 463 (CCPA 1976) (emphasis in the original); see also MPEP § 2111.03. Thus, the term "consisting essentially of" when used in a claim of this invention is not intended to be interpreted to be equivalent to "comprising."

Unless otherwise defined, all technical terms used herein have the same meaning as commonly understood by one of ordinary skill in the art to which this disclosure belongs.

As used herein, the term "subject" and "patient" are used interchangeably herein and refer to both human and nonhuman animals. A subject of this invention can be any subject that is susceptible to oral mucositis associated with radiation therapy and/or chemotherapy and/or conditioning therapy for HSCT, and in particular embodiments, the subject of this invention is a human subject.

A "subject in need thereof" or "a subject in need of" is a subject known to have, or is suspected of having or developing oral mucositis associated with radiation therapy and/or chemotherapy and/or conditioning therapy for HSCT. In particular embodiments, the subject is in need of, is scheduled for and/or is planning to undergo radiation and/or chemotherapy and/or conditioning therapy for HSCT, and/or other cancer treatment.

The term "administering" or "administered" as used herein is meant to include topical, parenteral and/or oral administration, all of which are described herein. Parenteral administration includes, without limitation, intravenous, subcutaneous and/or intramuscular administration (e.g., skeletal muscle or cardiac muscle administration). It will be appreciated that the actual method and order of administration will vary according to, inter cilia, the particular preparation of compound(s) being utilized, and the particular formulation(s) of the one or more other compounds being utilized. The optimal method and order of administration of the compounds of the invention for a given set of conditions can be ascertained by those skilled in the art using conventional techniques and in view of the information set out herein.

The term "administering" or "administered" also refers, without limitation, to oral, sublingual, buccal, transnasal, transdermal, rectal, intramuscular, intravenous, intraarterial (intracoronary), intraventricular, intrathecal, and subcutaneous routes. In accordance with good clinical practice, the instant compounds can be administered at a dose that will produce effective beneficial effects without causing undue harmful or untoward side effects, i.e., the benefits associated with administration outweigh the detrimental effects.

Also as used herein, the terms "treat," "treating" or "treatment" refer to any type of action that-imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, and/or change in clinical parameters of the condition, disorder, disease or illness, etc., as would be well known in the art.

Additionally, as used herein, the terms "prevent," "preventing" or "prevention" refer to any type of action that results in the absence, avoidance and/or delay of the onset and/or progression of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

As used herein, the term "ameliorate" refers to the ability to make better or more tolerable, a condition such as oral mucositis associated with radiation therapy and/or chemotherapy and/or conditioning therapy for HSCT. In some embodiments, the term "prevent" refers to the ability to keep a condition such as oral mucositis associated with radiation therapy and/or chemotherapy and/or conditioning therapy for HSCT from happening or existing as well as to diminish or delay onset. In some embodiments, the term "treating" refers to the caring for, or dealing with, a condition such as oral mucositis associated with radiation therapy and/or chemotherapy and/or conditioning therapy for HSCT.

Oral mucositis is inflammation of the mucous membrane in the mouth. For those suffering from oral mucositis, it is very important to have a good oral hygiene routine. Other self-care treatments include avoiding certain foods and drinks, sucking on ice cubes or ice chips, taking painkillers in the form of a mouth rinse, gel or spray, or taking palifermin.

Infection treatments may include antibiotics, antifungal, and/or antiviral medications. Oral cryotherapy (e.g. ice in the mouth) can also be employed prior to, during and/or following radiation therapy and/or chemotherapy and/or conditioning therapy for HSCT.

Patients receiving aggressive cancer therapies typically need aggressive nutrition management to help with nutritional compromise.

An "effective amount" or "therapeutically effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature and/or by using routine experimentation. (See, for example, Remington, *The Science and Practice of Pharmacy* (latest edition)).

Pharmaceutical compositions may be prepared as medicaments to be administered in any method suitable for the subject's condition, for example, orally, parenterally (including subcutaneous, intramuscular, and intravenous), rectally, transdermally, buccally, or nasally, or may be delivered directly to the heart by injection and/or catheter, or may be delivered to the eye as a liquid solution.

"Pharmaceutically acceptable," as used herein, means a material that is not biologically or otherwise undesirable, i.e., the material may be administered to a subject along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science*; latest edition). Exemplary pharmaceutically acceptable carriers for the compositions of this invention include, but are not limited to, sterile pyrogen-free water and sterile pyrogen-free physiological saline solution, as well as other carriers suitable for injection into and/or delivery to a subject of this invention, particularly a human subject, as would be well known in the art.

Suitable forms for oral administration include, but are not limited to, tablets, powders, compressed or coated pills, dragees, sachets, hard or gelatin capsules, sub-lingual tablets, syrups, and suspensions. Suitable forms of parenteral administration include, but are not limited to, an aqueous or non-aqueous solution or emulsion. Suitable forms for rectal administration, include, but are not limited to, suppositories with hydrophilic or hydrophobic vehicles. For topical administration, suitable forms include, but are not limited to, suitable transdermal delivery systems known in the art, such as patches, and for nasal delivery, suitable forms include, but are not limited to, aerosol and nebulized delivery systems known in the art.

A composition of the present invention (e.g., a pharmaceutical composition) may contain one or more excipients or adjuvants. Selection of excipients and/or adjuvants and the amounts to use may be readily determined by the formulation scientist upon experience and consideration of standard procedures and reference works in the field.

By "parenteral" is meant intravenous, subcutaneous or intramuscular administration. In the methods of the present invention, the composition or compound may be administered alone, simultaneously with one or more other compounds, or the composition and/or compounds may be administered sequentially, in either order. It will be appreciated that the actual method and order of administration will vary according to, inter alia, the particular preparation of compound(s) being utilized, the particular formulation(s) of the one or more other compounds being utilized, and the conditions to be treated. The optimal method and order of administration of the compounds of the disclosure for a given set of conditions can be ascertained by those skilled in the art using conventional techniques and in view of the information set out herein.

In prophylactic applications, pharmaceutical compositions or medicaments are administered to a subject susceptible to, or otherwise at risk of, occlusion or narrowing of an artery and/or its branches and/or a disease, disturbance and/or pathological condition of an artery and/or its branches in an amount sufficient to eliminate or reduce the risk, lessen the severity, or delay the onset, including biochemical, histologic and/or physiologic symptoms. In therapeutic applications, compositions or medicants are administered to a subject suspected of, or already having, occlusion or narrowing of an artery and/or its branches and/or has had or is having a disease, disturbance and/or pathological condition of an artery and/or its branches in an amount sufficient to treat, or at least partially reduce or arrest, the symptoms (biochemical, histologic and/or physiological). An amount adequate to accomplish therapeutic or prophylactic treatment is defined as an effective amount or a therapeutically or prophylactically effective dose. In either prophylactic or therapeutic regimens, compounds and/or compositions of the present invention can be administered in several doses until a desired effect has been achieved.

An effective dose or effective doses of the compositions of the present invention, for the treatment of the conditions described herein can vary depending upon many different factors, including means of administration, target site, physiological state of the subject, whether the subject is human or an animal, other medications administered, and/or whether treatment is prophylactic or therapeutic. In some embodiments, the subject is a human but nonhuman mammals including transgenic mammals can also be treated. Treatment dosages can be titrated to optimize safety and efficacy. Generally, an effective amount of the compositions of this invention will be determined by the age, weight and condition or severity of disease or disorder of the subject.

Generally, dosing (e.g., an administration) can be one or more times daily, or less frequently, such as once a day, once a week, once a month, once a year, to once in a decade, etc. and may be in conjunction with other compositions as described herein.

The dosage and frequency of administration can vary depending on whether the treatment is prophylactic or therapeutic. In prophylactic applications, a relatively low dosage can be administered at relatively infrequent intervals over a long period of time. In therapeutic applications, a relatively high dosage at relatively short intervals is sometimes appropriate until severity of the injury is reduced or terminated, and typically until the subject shows partial or complete amelioration of symptoms of injury. Thereafter, the subject can be administered a prophylactic regimen.

The terms "increased risk" and "decreased risk" as used herein define the level of risk that a subject has of having or developing oral mucositis as described herein, as compared to a control subject.

A sample of this invention can be cells, tissue and/or fluid (e.g., saliva, buccal swab, salivary gland tissue, etc.) from the oral cavity of a subject, as well as any other biological material from the subject that can be used to identify the genetic marker profile of the subject.

The present invention further provides a kit of reagents that can be used in the methods of this invention to determine the presence or absence of an allele of this invention in a DNA sample.

As will be understood by one skilled in the art, there are several embodiments and elements for each aspect of the claimed invention, and all combinations of different elements are hereby anticipated, so the specific combinations exemplified herein are not to be construed as limitations in the scope of the invention as claimed. If specific elements are removed or added to the group of elements available in a combination, then the group of elements is to be construed as having incorporated such a change.

The present invention is more particularly described in the following examples that are intended as illustrative only since numerous modifications and variations therein will be apparent to those skilled in the art.

EXAMPLES

Example 1. Conditioning Therapy-Induced Oral Mucositis Associated Single Nucleotide Polymorphisms (SNPs) Identified by Exome Sequence Analysis: A Pilot Study Using exome-sequencing, our objective was to identify candidate SNPs associated with oral mucositis (OM) in hematopoietic stem cell transplantation (HSCT) patients.

Saliva DNA was extracted from HSCT patients (n=63) with WHO-OM scores 2-4 (Group-2-4; n=24), or 0-1 (Group-0-1; n=39). Illumina HiSeq2000-paired-end platform was used for exome-sequencing. SNP calling was determined with GATK pipeline. Using a simplified logit model, ruling out that severity of OM would be solely associated with the intensity of conditioning treatment, a list of 309 SNPs/209 genes was obtained (uncorrected p-value<0.01). Assuming a "toxic gain in function", homozygous variant alleles overrepresented by more than 20% in Group-2-4 (possibly representing true positives independent from diagnosis) were determined. Proportions differences were evaluated by two-tailed 2-sample z-test.

Ten genes with SNP(s) were identified, including LAMC1 and ABCA4. LAMC1, essential for basal cell adhesion, had 8 SNPs that encompass 28 kbp. All SNPs combined were either heterozygous or homozygous for reference or variant genotype. Ten patients, eight in Group-2-4 and one with WHO-OM score 1, had variant homozygous genotype in LAMC1. Also, an overrepresented intronic homozygous SNP variant (100% penetrance) was found in ABCA4, a gene adjacent to ARHGAP29 gene. In a previous cleft lip/palate association study, a different intronic SNP in ABCA4 was found within a long distance regulatory element of ARHGAP29. ARHGAP29 is critical for craniofacial development and involved in oral epithelial cell adhesion.

Exome sequencing has potential to uncover SNPs relevant to oral mucositis.

Example 2. Conditioning Therapy-Induced Oral Mucositis-Associated Single Nucleotide Polymorphisms (SNPs) Identified by Exome Sequencing Analysis We have identified a set of ten candidate genes containing single nucleotide polymorphisms associated with a high incidence and moderate to high severity of oral mucositis (OM) following conditioning therapy of hematologic cancer patients prior to hematopoietic stem cell transplant (HSCT).

The idea of the study was to determine candidate genes that will demonstrate an increased risk for the development of severe mucositis in hematologic cancer and immunodeficient patients following conditioning therapy and prior to stem cell transplant. In our lab, we have received saliva samples from CMC, Sweden and Canada and have designed genomic studies to sequence the exome regions of the genomes using next generation sequencing.

Briefly, for analysis of the sequencing data, we have used a data analysis method that has not been described in the multi-center protocol. We ranked the results according to severity and looked for the significant single nucleotide polymorphisms (SNPs), and looked for their penetrance in the "2 to 4" WHO score "moderate to severe group" compared to the "0-1" score "none to low group."

We found SNPs in 10 genes out of list of 209 candidate genes (uncorrected p value<0.01) coming from the raw exome SNP data for 63 patients.

For these SNPs, we determined that if one patient had one of these mutations on the two parental chromosomes, there was a 70-100% chance for this patient to get moderate to severe oral mucositis. We are still working on getting data for a larger sample size to see how these odds would change, especially for the six genes that were 100% predictive. Also, there was no evidence of a correlation with the type of hematologic cancer, since these mutations hit all the cancer types we analysed (except one type for which we only had one patient). The biomarkers we identified appear to be independent of the type of cancer and conditioning regime (chemotherapy with or without radiation), based on the preliminary data we have for 63 patients.

Upon confirmation of these results for a larger population, we could develop a diagnostic test to let the patient know about the risks and determine preventive treatment approaches that are more aggressive before the cancer conditioning therapy is started and/or during such therapy.

Statistical Model for Mucositis Genetic Association

Instead of using the marginal or classical "logit" logistic regression model, a conditional logit model was used (conditioned on myeloablative chemotherapy group c=1 versus non-myeloablative group c=0)

$$\text{Logit}[P(M=1|c=1)]=\alpha+\beta g$$

Variables in the model are:
M: Mucositis grade (M=0, 1) (M=0: Low mucositis group OM score Group 0-1; M=1:
Moderate to severe mucositis OM score Group 2-4)
g: genotype or SNV at a specific locus, i.e., dose of the minor allele (g=0, 1, 2) (ref/ref, alt/ref, alt/alt)
c: chemotherapy group (c=0, 1)

The model was fitted to estimate the coefficients $\alpha$ and $\beta$, with $\beta$ indicating the effect (direction and magnitude) of the genotype or SNV (single nucleotide variant corresponding to single nucleotide polymorphisms or indels [insertions/deletions]) on mucositis. From the fitted model, we also determined whether $\beta$ is significantly different from 0 (null hypothesis H0: $\beta$=0), or whether the SNV is associated with mucositis. We obtained about 200,000 SNVs called in the Exome Sequencing data of the 63 patients. Most of these SNV are non-informative since these do not present much variability between different patients. Therefore, only ~73,000 informative SNVs were included in the model, thereby reducing the number of false positives. A total of 309 intragenic SNVs corresponding to 209 genes, potentially associated with mucositis (uncorrected p-value <0.01), were identified.

Secondary Analysis to Identify Potential True Positives.

Assuming a "toxic gain in function," homozygous variant alleles overrepresented by more than 20% in Group-2-4 (possibly representing true positives independent from diagnosis) were determined. Proportions differences were evaluated by two-tailed 2-sample z-test and the penetrance was determined for the genes with significant >20% change in proportion of the homozygous variant allele. We identified the following ten genes that had SNVs meeting the criteria. Genes with most discriminatory SNPs are shown in bold.

approaches are used to determine candidate genes (e.g., determine a genetic marker profile for a subject and/or population of subjects) that will demonstrate an increased risk for the development of severe mucositis (WHO grade 3 or 4) and determine the genes' function in developing OM. Genomic approaches may include the use of sequence analysis methods (e.g., SNP Arrays, Exome sequencing and/or other Next Generation Sequencing methods) for the determination of mutations (SNPs, indels [insertions/deletions], copy number variations [CNVs]), and/or the use of DNA methylation analytical methods (e.g., Infinium HumanMethylation450 Illumina BeadChip). This will provide preliminary data to achieve a power of 80%. In some embodiments, at least 2000 samples may be obtained to identify mutations associated with susceptibility to OM considering an effect size between 1.3 and 1.6. DNA libraries which will guide future functional genomic studies may also be developed.

Example 3. Targeted Allelic Sequencing Validation of Conditioning Therapy-Induced Oral Mucositis-Associated Single Nucleotide Polymorphisms (SNPs) Identified by Exome Sequencing Introduction. Oral mucositis (OM) is a common dose-limiting side effect of conditioning therapy for patients with hematologic cancer undergoing hematopoietic stem cell transplant (HSCT). Using exome sequencing in a pilot study, we have previously identified nine genes with SNPs associated with OM in HSCT patients. Our objective was to validate the candidate SNPs using targeted allelic sequencing.

Methods. Saliva DNA from HSCT patients (n=63), which was previously analyzed by whole genome exome sequencing, was subjected to targeted allelic sequencing for nine candidate genes. Sequencing was performed by Illumina HiSeq TruSeq paired-end sequencing of PCR amplicons of the targeted regions. SNPs/INDELS were identified using basic variant detection model within CLC Genomics Server software v9.0.1.

Results. Of the nine genes, LAMC1 had eight SNP locations which were either all heterozygous or homozygous for 56 out of the 63 patients. The full homozygote variant genotype was overrepresented in patients with OM WHO score 1-4. While targeted allelic sequencing confirmed the genotypes for the 56 patients, of the 16 ambiguous SNP

| Gene # | Symbol | | | | | Risk | | | |
|---|---|---|---|---|---|---|---|---|---|
| 1 | ABCA4 | rs4847278 | | | | G/G | | | |
| 2 | LAMC1 | rs10797854 | rs20560 | rs944970 | rs1062044 | G/G | G/G | C/C | C/C |
|   | LAMC1 | rs944971 | rs6424888 | rs20563 | rs2333620 | A/A | G/G | C/C | C/C |
| 3 | ORM1 | rs147960186 | | | | G/G | | | |
| 4 | COPB2 | rs7373116 | | | | A/A | | | |
| 5 | ACTL7B | rs11787880 | | | | G/G | | | |
| 6 | FBXO10 | rs10973387 | | | | A/A | | | |
| 7 | SF3B6 | rs61742149 | | | | G/A | | | |
| 8 | MRPS22 | rs10935321 | | | | A/A | | | |
| 9 | FAAH2 | rs4030473 | rs5915052 | | | A/A | G/G | | |
| 10 | MIR548I2 | rs111482845 | rs11728441 | | | T/T | T/T | | |

Saliva samples for functional genomic studies.

DNA saliva samples are obtained from patients prior to a conditioning regimen for autologous or allogeneic stem cell transplantation. These patients are followed prospectively to document the incidence and severity of mucositis. Genomic locations for remaining seven patients, 11 were corrected per conserved pattern. Indeed, one patient (WHO score=1), who had five ambiguous SNP locations in LAMC1, was confirmed having the full homozygote variant genotype. While SNP correction was related to low DNA concentration, non-correction was associated with lower DNA quality. Overall accuracy for the nine genes, including 13 corrections, was 99.3%.

Conclusions. Targeted allelic sequencing is an effective approach for confirming select SNPs prior to engaging into large sample size investigation of SNPs associated with OM in HSCT patients.

The foregoing is illustrative of the present invention, and is not to be construed as limiting thereof. The invention is defined by the following claims, with equivalents of the claims to be included therein. All publications, patent applications, patents, patent publications, sequences identified by GenBank and/or SNP and/or EntrezID and/or any other accession numbers, and other references cited herein are incorporated by reference in their entireties for the teachings relevant to the sentence and/or paragraph in which the reference is presented.

List of 309 intragenic SNVs and 209 corresponding genes:

| ENTREZID | SYMBOL | beta | p.val | CHROM | ID | REF | ALT |
|---:|---|---:|---:|---|---|---|---|
| 4735 | SEP12 | −2.5767083 | 0.0099746 | chr2 | rs12477089 | C | A |
| 24 | ABCA4 | 2.9708532 | 0.0029697 | chr1 | rs2297634 | T | C |
| 24 | ABCA4 | 2.8819911 | 0.0039517 | chr1 | rs4847278 | A | G |
| 4363 | ABCC1 | −2.7692145 | 0.0056192 | chr16 | rs246232 | C | G |
| 125981 | ACER1 | 2.9370196 | 0.0033138 | chr19 | rs72981971 | T | C |
| 10880 | ACTL7B | −3.0206808 | 0.0025221 | chr9 | rs11787880 | A | G |
| 10880 | ACTL7B | 2.8236865 | 0.0047475 | chr9 | rs3750469 | T | C |
| 170689 | ADAMTS15 | −2.7329452 | 0.0062771 | chr11 | rs731446 | T | C |
| 105 | ADARB2 | 2.8537339 | 0.0043209 | chr10 | rs4880498 | T | G |
| 84435 | ADGRA1 | 2.5919747 | 0.0095427 | chr10 | rs9419103 | C | T |
| 222611 | ADGRF2 | 2.5979603 | 0.0093779 | chr6 | rs10948375 | C | T |
| 222487 | ADGRG3 | −2.8196435 | 0.0048077 | chr16 | rs12444859 | C | T |
| 84059 | ADGRV1 | 2.6418998 | 0.0082442 | chr5 | rs41308293 | A | T |
| 3267 | AGFG1 | 3.1755816 | 0.0014954 | chr2 | rs4402755 | A | T |
| 8659 | ALDH4A1 | −2.7495943 | 0.0059669 | chr1 | rs4592275 | G | A |
| 51321 | AMZ2 | 2.6265541 | 0.0086254 | chr17 | rs3213690 | A | G |
| 286 | ANK1 | −2.8625479 | 0.0042025 | chr8 | rs7826127 | T | C |
| 286 | ANK1 | −2.7174232 | 0.0065792 | chr8 | rs2304883 | G | A |
| 286 | ANK1 | −2.5928753 | 0.0095177 | chr8 | rs2304871 | G | A |
| 80831 | APOL5 | 2.9853959 | 0.0028321 | chr22 | rs2076673 | C | G |
| 80831 | APOL5 | 2.8557877 | 0.004293 | chr22 | rs2076671 | C | T |
| 9411 | ARHGAP29 | 2.6815259 | 0.0073287 | chr1 | rs1048854 | T | C |
| 10620 | ARID3B | −2.85784 | 0.0042654 | chr15 | . | TACAC | TAC,T |
| 84239 | ATP13A4 | −2.6642603 | 0.0077158 | chr3 | rs61401139 | G | A |
| 10079 | ATP9A | −2.7320009 | 0.0062951 | chr20 | rs2255341 | C | T |
| 8313 | AXIN2 | 2.6609294 | 0.0077925 | chr17 | rs28760438 | A | G |
| 8313 | AXIN2 | 2.6609294 | 0.0077925 | chr17 | rs1133683 | G | A |
| 135152 | B3GAT2 | 2.6167767 | 0.0088764 | chr6 | rs1320315 | T | C |
| 145173 | B3GLCT | −2.8012546 | 0.0050904 | chr13 | rs9564692 | C | T |
| 60468 | BACH2 | 2.6617085 | 0.0077745 | chr6 | rs10455512 | T | C |
| 100129094 | BTNL10 | 2.6349379 | 0.0084153 | chr1 | rs6665115 | T | C |
| 64897 | C12orf43 | −2.5887247 | 0.0096332 | chr12 | rs2464195 | G | A |
| 64897 | C12orf43 | −2.5887247 | 0.0096332 | chr12 | rs2259816 | G | T |
| 388381 | C17orf98 | −2.6659294 | 0.0076776 | chr17 | rs597234 | G | A |
| 57545 | CC2D2A | −2.6665465 | 0.0076635 | chr4 | rs28419165 | C | T |
| 374864 | CCDC178 | −3.1703586 | 0.0015225 | chr18 | rs8087168 | A | T,* |
| 84960 | CCDC183 | 2.6561146 | 0.0079047 | chr9 | rs2784042 | T | C |
| 79741 | CCDC7 | 2.7106764 | 0.0067146 | chr10 | rs1977606 | C | G,CGG,* |
| 80381 | CO276 | 2.5807237 | 0.0098593 | chr15 | rs11574495 | G | A |
| 8881 | CDC16 | −2.7495943 | 0.0059669 | chr13 | rs8002514 | G | A |
| 8881 | CDC16 | −2.7495943 | 0.0059669 | chr13 | rs17337828 | AT | A |
| 8881 | CDC16 | −2.7495943 | 0.0059669 | chr13 | rs373731427 | TGCATCTC TTAAATA TGTGTGA (SEQ ID NO:1) | T |
| 5218 | CDK14 | −2.6918616 | 0.0071054 | chr7 | rs3814097 | G | A |
| 1057 | CELP | 2.6507605 | 0.0080311 | chr9 | rs640502 | G | A |
| 84131 | CEP78 | −2.8966494 | 0.0037717 | chr9 | rs10867166 | G | C |
| 84131 | CEP78 | −2.8966494 | 0.0037717 | chr9 | rs13292584 | G | A |
| 84131 | CEP78 | −2.6329381 | 0.008465 | chr9 | rs11137579 | C | T |
| 9076 | CLDN1 | −2.5819011 | 0.0098258 | chr3 | rs17500920 | T | A |
| 79745 | CLIP4 | −2.692565 | 0.0070905 | chr2 | rs3213947 | A | G |
| 80790 | CMIP | −2.7056145 | 0.0068178 | chr16 | rs4889356 | A | G |
| 26047 | CNTNAP2 | 2.6246144 | 0.0086747 | chr7 | rs2074715 | A | G |
| 150684 | COMMD1 | −2.6329381 | 0.008465 | chr2 | rs67059162 | G | A |
| 9276 | COPB2 | 2.6856931 | 0.007238 | chr3 | rs7373116 | G | A |
| 1379 | CR1L | −3.1424532 | 0.0016754 | chr1 | rs2296158 | A | G |
| 51232 | CRIM1 | −3.2737649 | 0.0010612 | chr2 | rs10181664 | C | T |
| 51232 | CRIM1 | −3.136271 | 0.0017111 | chr2 | rs10180760 | T | G |
| 51232 | CRIM1 | −2.9913185 | 0.0027778 | chr2 | rs10178965 | G | A |
| 51232 | CRIM1 | −2.9366696 | 0.0033176 | chr2 | rs1533946 | T | C |
| 51232 | CRIM1 | −2.7385584 | 0.0061709 | chr2 | rs10194100 | T | C |
| 23191 | CYFIP1 | −3.0916991 | 0.0019901 | chr15 | rs3217548 | AC | A |
| 91351 | DDX60L | −2.6432183 | 0.0082122 | chr4 | rs34009039 | G | GT,GTT |

List of 309 intragenic SNVs and 209 corresponding genes:

| ENTREZID | SYMBOL | beta | p.val | CHROM | ID | REF | ALT |
|---|---|---|---|---|---|---|---|
| 55526 | DHTKD1 | 2.6113789 | 0.0090178 | chr10 | rs12416681 | G | A |
| 27122 | DKK3 | 2.7309057 | 0.0063161 | chr11 | rs67506856 | C | A |
| 27120 | DKKL1 | 2.6837226 | 0.0072807 | chr19 | rs11421569 | A | AG |
| 1741 | DLG3 | 2.7555526 | 0.0058593 | chrX | rs3811371 | A | G |
| 127602 | DNAH14 | 3.1179197 | 0.0018213 | chr1 | rs630120 | T | C |
| 127602 | DNAH14 | 3.1179197 | 0.0018213 | chr1 | rs670255 | G | T |
| 1793 | DOCK1 | 2.6658964 | 0.0076783 | chr10 | rs2296636 | C | T |
| 9980 | DOPEY2 | −2.9826662 | 0.0028575 | chr21 | rs9977791 | C | T |
| 9980 | DOPEY2 | −2.9826662 | 0.0028575 | chr21 | rs9978057 | G | A |
| 9980 | DOPEY2 | 2.7309057 | 0.0063161 | chr21 | rs58117793 | A | AT |
| 23167 | EFR3A | 2.6744301 | 0.0074856 | chr8 | rs2270875 | A | G |
| 23167 | EFR3A | 2.6744301 | 0.0074856 | chr8 | rs8859 | C | G |
| 2041 | EPHA1 | −3.2439307 | 0.0011789 | chr7 | rs45497499 | A | G |
| 2041 | EPHA1 | −3.085143 | 0.0020345 | chr7 | rs1131885 | T | C |
| 285965 | EPHA1-AS1 | 2.7595525 | 0.0057881 | chr7 | rs117188605 | G | A |
| 2066 | ERBB4 | −2.8015873 | 0.0050852 | chr2 | rs141267844 | G | GT |
| 220081 | ERICH6B | −2.7692145 | 0.0056192 | chr13 | rs1536207 | C | A |
| 56605 | ERO1B | 2.6663347 | 0.0076683 | chr1 | rs1269025 | C | T |
| 2099 | ESR1 | −3.0029226 | 0.002674 | chr6 | rs1801132 | G | C |
| 2131 | EXT1 | 2.5988812 | 0.0093528 | chr8 | rs17439693 | G | A |
| 2138 | EYA1 | −2.7204359 | 0.0065196 | chr8 | rs7846086 | G | A |
| 2138 | EYA1 | −2.7204359 | 0.0065196 | chr8 | rs3735935 | C | A |
| 158584 | FAAH2 | 2.9244829 | 0.0034503 | chrX | rs5915052 | T | G |
| 158584 | FAAH2 | 2.8655162 | 0.0041633 | chrX | rs4030473 | T | A |
| 221061 | FAM171A1 | 2.7991092 | 0.0051244 | chr10 | rs6602828 | C | T |
| 221061 | FAM171A1 | 2.6744301 | 0.0074856 | chr10 | rs3814165 | G | A |
| 23116 | FAM179B | 2.5919747 | 0.0095427 | chr14 | . | AT | A,ATT |
| 26267 | FBXO10 | 2.5781364 | 0.0099335 | chr9 | rs10973387 | G | A |
| 654463 | FER1L6 | 2.5781364 | 0.0099335 | chr8 | rs7820272 | G | A |
| 9637 | FEZ2 | −3.1489465 | 0.0016386 | chr2 | rs2072533 | A | G |
| 9637 | FEZ2 | −3.136271 | 0.0017111 | chr2 | rs2072534 | G | A |
| 9637 | FEZ2 | −3.0965273 | 0.001958 | chr2 | rs11691767 | G | T |
| 9637 | FEZ2 | −3.0561234 | 0.0022422 | chr2 | rs848638 | C | T |
| 9637 | FEZ2 | −2.8753906 | 0.0040353 | chr2 | rs14291 | T | C |
| 221472 | FGD2 | 2.738796 | 0.0061665 | chr6 | rs75479065 | C | CT |
| 121512 | FGD4 | 2.5930064 | 0.0095141 | chr12 | . | CT | CTT,C,CTTT |
| 2322 | FLT3 | 2.867619 | 0.0041357 | chr13 | rs61944200 | C | T |
| 2322 | FLT3 | 2.6861202 | 0.0072287 | chr13 | rs9581971 | C | T |
| 79025 | FNDC11 | −2.8966494 | 0.0037717 | chr20 | rs3746348 | T | C |
| 79025 | FNDC11 | −2.7976388 | 0.0051478 | chr20 | rs734750 | T | C |
| 202309 | GAPT | −2.7811431 | 0.0054168 | chr5 | rs7704785 | T | C |
| 202309 | GAPT | −2.7811431 | 0.0054168 | chr5 | rs1389308 | T | G |
| 220032 | GDPD4 | 2.5881572 | 0.0096491 | chr11 | rs4945161 | G | A |
| 390637 | GDPGP1 | 3.1318335 | 0.0017372 | chr15 | rs8025610 | G | C |
| 390637 | GDPGP1 | 2.9409025 | 0.0032726 | chr15 | rs10153004 | C | T |
| 2733 | GLE1 | 3.5275981 | 0.0004193 | chr9 | rs2275260 | A | G |
| 59345 | GNB4 | −2.6317543 | 0.0084945 | chr3 | rs3774225 | C | T |
| 2982 | GUCY1A3 | 2.8970065 | 0.0037674 | chr4 | rs3796585 | G | A |
| 2982 | GUCY1A3 | 2.7516233 | 0.0059301 | chr4 | rs2306555 | T | A |
| 3037 | HAS2 | −2.7148821 | 0.0066299 | chr8 | rs2028506 | G | C |
| 55355 | HJURP | −2.6152191 | 0.008917 | chr2 | rs2286430 | C | T |
| 64342 | HS1BP3 | −2.7998216 | 0.0051131 | chr2 | rs10186292 | C | A |
| 64342 | HS1BP3 | −2.729085 | 0.006351 | chr2 | rs2305460 | G | A,T |
| 283284 | IGSF22 | 2.738796 | 0.0061665 | chr11 | rs7106673 | G | A |
| 283284 | IGSF22 | 2.738796 | 0.0061665 | chr11 | rs7125943 | T | C |
| 283284 | IGSF22 | 2.738796 | 0.0061665 | chr11 | rs4424652 | C | T |
| 283284 | IGSF22 | 2.738796 | 0.0061665 | chr11 | rs10766494 | C | T |
| 22806 | IKZF3 | −2.7901787 | 0.0052679 | chr17 | rs1453559 | T | C |
| 27178 | IL37 | 3.0531476 | 0.0022645 | chr2 | rs3811047 | A | G |
| 27178 | IL37 | 2.6552232 | 0.0079256 | chr2 | rs3811045 | T | C |
| 27178 | IL37 | 2.6552232 | 0.0079256 | chr2 | rs3811046 | G | T |
| 359948 | IRF2BP2 | −2.792731 | 0.0052265 | chr1 | rs4636 | C | A |
| 3689 | ITGB2 | 2.735279 | 0.0062327 | chr21 | rs7282201 | G | A |
| 100505746 | ITGB2-AS1 | 2.735279 | 0.0062327 | chr21 | rs12483718 | C | G |
| 23189 | KANK1 | −2.6730359 | 0.0075168 | chr9 | rs10125507 | G | A |
| 25962 | KIAA1429 | −2.7831611 | 0.0053832 | chr8 | rs1866844 | T | C |
| 57614 | KIAA1468 | 3.3453216 | 0.0008219 | chr18 | . | CT | C,CTT |
| 85379 | KIAA1671 | −2.6702525 | 0.0075794 | chr22 | rs763279 | G | A |
| 85379 | KIAA1671 | 2.6541057 | 0.0079519 | chr22 | rs2330986 | T | G |
| 9585 | KIF20B | 3.269783 | 0.0010763 | chr10 | rs11185853 | G | A |
| 9585 | KIF20B | 3.2148563 | 0.0013051 | chr10 | N144593231 | C | CTAAAAG |
| 9585 | KIF20B | 3.1613754 | 0.0015703 | chr10 | rs10881648 | G | T |
| 9585 | KIF20B | 3.1613754 | 0.0015703 | chr10 | rs2026549 | A | G |
| 9585 | KIF20B | 3.1613754 | 0.0015703 | chr10 | rs3824609 | T | C |
| 9585 | KIF20B | 3.0474634 | 0.0023078 | chr10 | rs7089473 | T | G |

-continued

List of 309 intragenic SNVs and 209 corresponding genes:

| ENTREZID | SYMBOL | beta | p.val | CHROM | ID | REF | ALT |
|---|---|---|---|---|---|---|---|
| 9585 | KIF20B | 3.0474634 | 0.0023078 | chr10 | rs8181361 | G | A |
| 9585 | KIF20B | 3.0474634 | 0.0023078 | chr10 | rs1062465 | T | A |
| 9585 | KIF20B | 3.0474634 | 0.0023078 | chr10 | rs1886997 | A | G |
| 9585 | KIF20B | 3.0474634 | 0.0023078 | chr10 | rs1126480 | A | G |
| 9585 | KIF20B | 3.0142257 | 0.0025764 | chr10 | rs3758389 | A | T |
| 9585 | KIF20B | 2.9111774 | 0.0036007 | chr10 | rs1048057 | A | C |
| 9585 | KIF20B | 2.591782 | 0.009548 | chr10 | rs10881632 | A | G |
| 55083 | KIF26B | −2.9279094 | 0.0034125 | chr1 | rs12409851 | C | T |
| 8609 | KLF7 | −2.9366696 | 0.0033176 | chr2 | rs2284934 | C | T |
| 8609 | KLF7 | −2.7385584 | 0.0061709 | chr2 | rs768090 | A | T |
| 387264 | KRTAP5-1 | −2.8643675 | 0.0041784 | chr11 | . | ACCACAGC CACCCTTG GATCCCCC ACAAGAG (SEQ ID NO:2) | A |
| 387264 | KRTAP5-1 | −2.5855687 | 0.0097219 | chr11 | rs80025267 | T | G,* |
| 3915 | LAMC1 | 2.9137985 | 0.0035706 | chr1 | rs10797854 | G | A |
| 3915 | LAMC1 | 2.9002164 | 0.0037291 | chr1 | rs20560 | T | C |
| 3915 | LAMC1 | 2.8375629 | 0.0045459 | chr1 | rs944970 | T | C |
| 3915 | LAMC1 | 2.7067296 | 0.006795 | chr1 | rs1062044 | A | G |
| 3915 | LAMC1 | 2.7067296 | 0.006795 | chr1 | rs944971 | T | C |
| 3915 | LAMC1 | 2.645959 | 0.008146 | chr1 | rs6424888 | A | G |
| 3915 | LAMC1 | 2.645959 | 0.008146 | chr1 | rs20563 | A | G |
| 3915 | LAMC1 | 2.6246144 | 0.0086747 | chr1 | rs2333620 | T | C |
| 3937 | LCP2 | 2.6113789 | 0.0090178 | chr5 | rs395407 | G | C |
| 3988 | LIPA | −2.7038647 | 0.0068538 | chr10 | rs1051338 | T | G |
| 643414 | LIPK | 3.0490129 | 0.0022959 | chr10 | rs415996 | T | G |
| 643414 | LIPK | 2.9738969 | 0.0029404 | chr10 | rs376036 | C | T |
| 643414 | LIPK | 2.9738969 | 0.0029404 | chr10 | rs432950 | C | T |
| 643414 | LIPK | 2.9738969 | 0.0029404 | chr10 | rs390414 | A | T |
| 643414 | LIPK | 2.9738969 | 0.0029404 | chr10 | rs406102 | C | A |
| 643414 | LIPK | 2.9738969 | 0.0029404 | chr10 | rs427687 | A | G |
| 643414 | LIPK | 2.8292695 | 0.0046654 | chr10 | rs11358016 | GA | G |
| 4005 | LMO2 | 2.6741038 | 0.0074929 | chr11 | rs2038602 | A | G |
| 80856 | LNPK | 2.8285266 | 0.0046763 | chr2 | rs935492 | C | T |
| 100506639 | LOC100506639 | −2.6347851 | 0.0084191 | chr5 | rs11748187 | C | T |
| 120892 | LRRK2 | 2.6418998 | 0.0082442 | chr12 | rs7966550 | T | C |
| 4046 | LSP1 | 2.6837289 | 0.0072806 | chr11 | rs2089910 | C | T |
| 28986 | MAGEH1 | 2.711683 | 0.0066943 | chrX | rs11545211 | G | A |
| 6885 | MAP3K7 | 2.6418998 | 0.0082442 | chr6 | . | G | GA |
| 4163 | MCC | 2.9111647 | 0.0036008 | chr5 | rs113825892 | GGTCACT GGGCA (SEQ ID NO:3) | G |
| 55669 | MFN1 | −2.6317543 | 0.0084945 | chr3 | rs73043490 | C | T |
| 125170 | MIEF2 | 2.8192567 | 0.0048135 | chr17 | rs80026520 | CCCT | C |
| 100302233 | MIR1268A | 3.4516155 | 0.0005572 | chr9 | rs869455 | G | T |
| 100302233 | MIR1268A | 2.9738969 | 0.0029404 | chr9 | rs3924786 | T | A |
| 442905 | MIR337 | 2.5879676 | 0.0096544 | chr14 | rs41286558 | G | A |
| 100302277 | MIR54812 | 2.8915656 | 0.0038333 | chr4 | rs111482845 | TAGAAGG | T |
| 100302277 | MIR54812 | 2.7261648 | 0.0064075 | chr4 | rs11728441 | T | C |
| 389690 | MROH5 | 2.7018075 | 0.0068964 | chr8 | rs2748421 | A | G |
| 389690 | MROH5 | 2.7018075 | 0.0068964 | chr8 | rs2613648 | C | T |
| 389690 | MROH5 | −2.7018075 | 0.0068964 | chr8 | rs11355664 | TG | T,TGG |
| 56945 | MRPS22 | 2.6856931 | 0.007238 | chr3 | rs10935321 | G | A |
| 84437 | MSANTD4 | 2.7193317 | 0.0065414 | chr11 | rs1043144 | C | T |
| 283463 | MUC19 | −2.9586724 | 0.0030897 | chr12 | rs11564168 | T | C |
| 283463 | MUC19 | −2.9586724 | 0.0030897 | chr12 | rs60890556 | C | CA |
| 283463 | MUC19 | −2.9160475 | 0.003545 | chr12 | rs7139187 | A | C |
| 283463 | MUC19 | −2.8978491 | 0.0037573 | chr12 | rs7971316 | G | C |
| 53904 | MYO3A | 2.7235946 | 0.0064576 | chr10 | rs16926628 | T | C |
| 53904 | MYO3A | 2.6805577 | 0.00735 | chr10 | rs17739680 | T | C |
| 4646 | MYO6 | 2.6418998 | 0.0082442 | chr6 | , | G | GA |
| 8736 | MYOM1 | 2.5979603 | 0.0093779 | chr18 | rs948298 | G | T |
| 89795 | NAV3 | 2.7235946 | 0.0064576 | chr12 | rs1731740 | G | C |
| 10725 | NFAT5 | 2.8575121 | 0.0042698 | chr16 | rs3826154 | A | G |
| 4843 | NOS2 | 2.9864431 | 0.0028224 | chr17 | rs2297518 | G | A |
| 64067 | NPAS3 | 2.9409025 | 0.0032726 | chr14 | rs3831102 | T | TC |
| 255743 | NPNT | 2.6156026 | 0.008907 | chr4 | rs6817700 | A | G |
| 2494 | NR5A2 | 2.7585031 | 0.0058067 | chr1 | rs117679244 | T | G,* |
| 203447 | NRK | 2.8329271 | 0.0046124 | chrX | rs58225635 | G | A |
| 203447 | NRK | 2.6090081 | 0.0090805 | chrX | rs209373 | G | A |
| 11164 | NUDT5 | 2.7554841 | 0.0058605 | chr10 | rs150891932 | GT | G,GTT |
| 11164 | NUDT5 | 2.7545414 | 0.0058774 | chr10 | rs2272207 | C | T |
| 128368 | OR10Z1 | 3.1066582 | 0.0018922 | chr1 | rs2427808 | A | T |

List of 309 intragenic SNVs and 209 corresponding genes:

| ENTREZID | SYMBOL | beta | p.val | CHROM | ID | REF | ALT |
|---|---|---|---|---|---|---|---|
| 401666 | 0R51A4 | 2.7595525 | 0.0057881 | chr11 | rs2605301 | A | G |
| 401666 | 0R51A4 | 2.735279 | 0.0062327 | chr11 | rs2595992 | G | T |
| 5004 | ORM1 | 2.9157173 | 0.0035487 | chr9 | rs147960186 | G | A |
| 29948 | OSGIN1 | 2.5879676 | 0.0096544 | chr16 | rs173776 | A | G |
| 8974 | P4HA2 | 2.9148398 | 0.0035587 | chr5 | rs154483 | A | G |
| 5058 | PAK1 | 2.6849305 | 0.0072545 | chr11 | rs51500 | C | T |
| 53354 | PANK1 | 2.9290917 | 0.0033995 | chr10 | rs11185826 | C | G |
| 5101 | PCDH9 | 2.7067296 | 0.006795 | chr13 | rs9571740 | G | A |
| 5138 | PDE2A | −2.5773855 | 0.0099551 | chr11 | rs1980091 | G | A |
| 5155 | PDGFB | −2.7398647 | 0.0061464 | chr22 | rs2239769 | C | T |
| 8863 | PER3 | 2.735279 | 0.0062327 | chr1 | rs10462021 | A | G |
| 8863 | PER3 | 2.6155844 | 0.0089075 | chr1 | rs2640909 | T | C |
| 5208 | PFKFB2 | 3.1154003 | 0.001837 | chr1 | rs2075863 | G | A |
| 55276 | PGM2 | 2.6054259 | 0.009176 | chr4 | rs3832307 | AT | A |
| 23035 | PHLPP2 | 2.6113789 | 0.0090178 | chr16 | rs61733127 | A | G |
| 118788 | PIK3AP1 | −2.5773855 | 0.0099551 | chr10 | rs3748231 | C | T |
| 283748 | PLA2G4D | −2.8978491 | 0.0037573 | chr15 | rs12906547 | T | G |
| 283748 | PLA2G4D | −2.8978491 | 0.0037573 | chr15 | rs11635685 | G | C |
| 283748 | PLA2G4D | −2.6659294 | 0.0076776 | chr15 | rs4924618 | A | T |
| 151056 | PLB1 | 3.1363171 | 0.0017108 | chr2 | rs1534478 | C | T |
| 57475 | PLEKHH1 | 2.7595525 | 0.0057881 | chr14 | rs3742873 | G | A |
| 119548 | PNLIPRP3 | 2.6617085 | 0.0077745 | chr10 | rs 10749217 | A | C |
| 55844 | PPP2R2D | −2.8734909 | 0.0040596 | chr10 | rs7894 | G | C |
| 5558 | PRIM2 | −2.5919747 | 0.0095427 | chr6 | rs73752376 | A | G |
| 26121 | PRPF31 | 2.5885668 | 0.0096376 | chr19 | rs45513391 | G | A |
| 23198 | PSME4 | −2.6606836 | 0.0077982 | chr2 | . | G | GA |
| 5794 | PTPRH | 2.6418998 | 0.0082442 | chr19 | rs111326663 | G | C |
| 5794 | PTPRH | 2.6418998 | 0.0082442 | chr19 | rs2288520 | G | A |
| 65997 | RASL11B | 2.6609294 | 0.0077925 | chr4 | rs11734439 | C | T |
| 5968 | REG1B | 2.5942684 | 0.0094792 | chr2 | rs2073445 | G | T |
| 84957 | RELT | 2.5885668 | 0.0096376 | chill | rs11826896 | C | T |
| 8796 | SCEL | 2.7383078 | 0.0061756 | chr13 | rs9574090 | T | C |
| 55681 | SCYL2 | 2.9566681 | 0.0031098 | chr12 | rs11110340 | A | T |
| 55176 | SEC61A2 | 2.7545414 | 0.0058774 | chr10 | rs3780860 | T | C |
| 26470 | SEZ6L2 | 2.7309057 | 0.0063161 | chr16 | rs11649499 | C | G |
| 51639 | SF3B6 | 2.5919747 | 0.0095427 | chr2 | rs61742149 | G | A |
| 84561 | SLC12A8 | −2.5859765 | 0.0097104 | chr3 | rs1574340 | A | G |
| 6570 | SLC18A1 | −2.5819011 | 0.0098258 | chr8 | rs2270637 | C | G |
| 9389 | SLC22A14 | 2.7098895 | 0.0067306 | chr3 | rs753330 | T | G |
| 5002 | SLC22A18 | 2.9480242 | 0.0031981 | chr11 | rs1048047 | G | A |
| 126969 | SLC44A3 | 3.1626232 | 0.0015635 | chr1 | rs17407097 | A | G |
| 126969 | SLC44A3 | 2.7991092 | 0.0051244 | chr1 | rs2640065 | T | C |
| 9498 | SLC4A8 | −2.6281702 | 0.0085846 | chr12 | rs10783448 | G | A |
| 113278 | SLC52A3 | −2.8966494 | 0.0037717 | chr20 | rs11273404 | A | ACAGGTCAAT (SEQ ID NO: 4) |
| 9152 | SLC6A5 | 2.9409025 | 0.0032726 | chr11 | rs1443548 | T | C |
| 9351 | SLC9A3R2 | −2.6730359 | 0.0075168 | chr16 | rs11876 | C | T |
| 140775 | SMCR8 | 2.8192567 | 0.0048135 | chr17 | rs12449313 | A | G |
| 140775 | SMCR8 | 2.8192567 | 0.0048135 | chr17 | rs2273029 | G | A |
| 23293 | SMG6 | −2.8184381 | 0.0048258 | chr17 | rs216196 | T | C |
| 26796 | SNORD53 | 2.9347033 | 0.0033387 | chr2 | rs9653591 | G | T |
| 26796 | SNORD53 | 2.6598962 | 0.0078165 | chr2 | rs34113296 | T | G |
| 51429 | SNX9 | −2.6809798 | 0.0073407 | chr6 | rs11324404 | GA | G |
| 51429 | SNX9 | −2.668953 | 0.0076088 | chr6 | rs3211067 | G | A |
| 80309 | SPHKAP | −2.8049331 | 0.0050327 | chr2 | rs4585022 | G | A |
| 80309 | SPHKAP | −2.6473672 | 0.0081121 | chr2 | rs4353646 | A | G |
| 6726 | SRP9 | 2.6460429 | 0.0081439 | chr1 | rs4653433 | A | G |
| 55808 | ST6GALNAC1 | −3.249793 | 0.0011549 | chr17 | rs2286595 | C | T |
| 55808 | ST6GALNAC1 | −3.0039956 | 0.0026646 | chr17 | rs719430 | T | C |
| 6489 | ST8S1A1 | −2.5819011 | 0.0098258 | chr12 | . | G | GA |
| 442038 | SULT1C3 | −2.7495943 | 0.0059669 | chr2 | rs9308806 | A | C |
| 26032 | SUSD5 | 2.735279 | 0.0062327 | chr3 | rs4257493 | G | A |
| 26032 | SUSD5 | 2.735279 | 0.0062327 | chr3 | rs61743511 | G | A |
| 23345 | SYNE1 | 2.7748317 | 0.005523 | chr6 | rs2296254 | C | T |
| 23345 | SYNE1 | 2.7748317 | 0.005523 | chr6 | rs36215566 | T | TA |
| 143425 | SYT9 | −2.7028692 | 0.0068744 | chr11 | rs2035639 | C | G |
| 23329 | TBC1D30 | 2.6113789 | 0.0090178 | chr12 | rs61730726 | A | G |
| 6929 | TCF3 | 2.5942684 | 0.0094792 | chr19 | rs1140828 | G | A |
| 8463 | TEAD2 | 2.6837226 | 0.0072807 | chr19 | rs2303758 | G | T |
| 83741 | TFAP2D | −2.7377615 | 0.0061859 | chr6 | rs3765306 | A | G |
| 57103 | TIGAR | −2.6230947 | 0.0087135 | chr12 | rs7296163 | T | C |

List of 309 intragenic SNVs and 209 corresponding genes:

| ENTREZID | SYMBOL | beta | p.val | CHROM | ID | REF | ALT |
|---|---|---|---|---|---|---|---|
| 8914 | TIMELESS | 2.9971308 | 0.0027253 | chr12 | rs66491720 | G | A |
| 10430 | TMEM147 | 2.8790953 | 0.0039882 | chr19 | rs7599 | A | G |
| 56674 | TMEM9B | 2.6633559 | 0.0077366 | chr11 | . | TAGGAAG | GAGGAAG,* |
| 7156 | TOP3A | 2.8192567 | 0.0048135 | chr17 | rs3817992 | C | A |
| 7156 | TOP3A | 2.8192567 | 0.0048135 | chr17 | rs2294913 | C | T |
| 127262 | TPRG1L | -2.699407 | 0.0069463 | chr1 | rs147637374 | GTTCTGGGAGCTCCTCCCCC (SEQ ID NO:5) | G |
| 162514 | TRPV3 | 2.7437543 | 0.0060741 | chr17 | rs322937 | T | C |
| 441631 | TSPAN11 | 2.6418998 | 0.0082442 | chr12 | rs11051187 | C | T |
| 54970 | TTC12 | 2.7664373 | 0.0056672 | chr11 | rs723078 | C | G |
| 145567 | TTC7B | -2.761318 | 0.0057569 | chr14 | rs10146731 | C | T |
| 9690 | UBE3C | -2.5767083 | 0.0099746 | chr7 | rs7807 | C | A |
| 29979 | UBQLN1 | -2.5767083 | 0.0099746 | chr9 | rs7866234 | C | A |
| 54576 | UGT1A8 | 2.9586092 | 0.0030903 | chr2 | rs6738678 | C | 1.* |
| 57663 | USP29 | 2.6805577 | 0.00735 | chr19 | rs9973206 | C | A |
| 7450 | VWF | 2.9566681 | 0.0031098 | chr12 | rs55867239 | G | A |
| 7450 | VWF | 2.9566681 | 0.0031098 | chr12 | rs1053523 | T | C |
| 7450 | VWF | -2.8015873 | 0.0050852 | chr12 | rs216902 | G | A |
| 23160 | WDR43 | 3.0439318 | 0.0023351 | chr2 | rs6715296 | C | G |
| 100131176 | WDR86-AS1 | 2.5899613 | 0.0095987 | chr1 | rs12533730 | C | T |
| 80014 | WWC2 | -3.2172997 | 0.001294 | chr4 | rs3814422 | G | C |
| 80014 | WWC2 | -3.0742807 | 0.0021101 | chr4 | rs2292414 | C | G |
| 51741 | WWOX | 2.6493809 | 0.0080639 | chr16 | rs2288034 | C | G |
| 51741 | WWOX | 2.6493809 | 0.0080639 | chr16 | rs2288033 | T | C |
| 55432 | YOD1 | 2.9036194 | 0.0036888 | chr1 | rs3790619 | T | G |
| 55432 | YOD1 | 2.8964843 | 0.0037737 | chr1 | rs2629665 | C | A |
| 29799 | YPEL1 | -2.7524989 | 0.0059142 | chr22 | rs2236643 | A | G |
| 7771 | ZNF112 | 2.6856931 | 0.007238 | chr19 | rs2609880 | T | G |
| 7771 | ZNF112 | 2.6856931 | 0.007238 | chr19 | rs2722723 | C | G |
| 7771 | ZNF112 | 2.6856931 | 0.007238 | chr19 | rs2571104 | T | C |
| 84911 | ZNF382 | 2.6186037 | 0.008829 | chr19 | rs3108171 | A | G |
| 90649 | ZNF486 | 2.6518891 | 0.0080043 | chr19 | rs836897 | C | G |
| 57711 | ZNF529 | 2.8192567 | 0.0048135 | chr19 | rs3108598 | T | C |
| 57711 | ZNF529 | 2.7261648 | 0.0064075 | chr19 | rs3096618 | C | T |
| 124626 | ZPBP2 | -2.7692145 | 0.0056192 | chr17 | rs11557467 | G | T |
| 54764 | ZRANB1 | 2.6636806 | 0.0077291 | chr10 | rs72416239 | ACGCGCGCGCG (SEQ ID NO:6) | ACG, ACGCG, ACGCGCG, ACGCGCGCG,A | z-scores for >20% variant allele predominance in Group 2-4 "HighMuc" versus Group 0-1 "LowMuc" for the ten genes:

| Gene 1 | ABCA4 | | |
|---|---|---|---|
| Entrez ID | 24 | | |
| Role | Adhesion | Intron Regulatory | |
| Polymorphism | rs4847278 | | |
| Reference REF | A | | |
| Variant ALT | G | | |
| | AA | AG | GG |
| LowMUC | 58.97% | 41.03% | 0.00% |
| HighMuc | 29.17% | 45.83% | 33.33% |
| Predominance | 29.81% | 33.33% | |
| | Sample 1 | Sample 2 | Difference |
| Sample proportion | 0 | 0.3333 | 0.3333 |
| 95% CI (asymptotic) | 0-0 | 0.1447-0.5219 | 0.164-0.5026 |
| z-value | 3.9 | | |
| P-value | 0.0001 | | |
| Interpretation | Statistically significant, reject null hypothesis that sample proportions are equal | | | z-scores for >20% variant allele predominance in Group 2-4 "HighMuc" versus Group 0-1 "LowMuc" for the ten genes:

| n by pi | n * pi <=5, test inappropriate | | | |
|---|---|---|---|---|
| Penetrance Group 2-4 OM score | 100% | | | |
| Penetrance OM score 1-4 | 100% | | | |

| Gene 2 | LAMC1 | | | |
|---|---|---|---|---|
| Entrez ID | 3915 | | | |
| Role | Adhesion | Intron Regulatory | | |
| Polymorphism | rs10797854 | rs20560 | rs944970 | rs1062044 |
| Reference REF | A | A | T | T |
| Variant ALT | G | G | C | C |
| Polymorphism | rs944971 | rs6424888 | r820563 | rs2333620 |
| Reference REF | G | A | T | T |
| Variant ALT | A | G | C | C |
| | AA | AG | GG | |
| LowMUC | 33.33% | 61.54% | 5.13% | |

| | | | |
|---|---|---|---|
| HighMuc | 8.33% | 58.33% | 33.33% |
| Predominance | 25.00% | | 28.21% |
| | Sample 1 | Sample 2 | Difference |
| Sample proportion | 0.0513 | 0.3333 | 0.282 |
| 95% CI (asymptotic) | −0.1384 | 0.1447-0.5219 | 0.0962-0.4678 |
| z-value | 3 | | |
| P-value | 0.0029 | | |
| Interpretation | Statistically significant, reject null hypothesis that sample proportions are equal | | |
| n by pi | n * pi <= 5, test inappropriate | | |
| Penetrance Group 2-4 OM score | 80% | | |
| Penetrance OM score 1-4 | 90% | | |

| | | | |
|---|---|---|---|
| Gene 3 | | ORM1 | |
| Entrez ID | 5004 | | |
| Role | Immunosuppression | Anti-Inflammatory | Coding missense |
| Polymorphism | | rs147960186 | |
| Reference | REF | G | |
| Variant | ALT | A | |
| | AA | AG | GG |
| LowMUC | 46.15% | 48.72% | 5.13% |
| HighMuc | 20.83% | 50.00% | 29.17% |
| Predominance | 25.32% | | 24.04% |
| | Sample 1 | Sample 2 | Difference |
| Sample proportion | 0.0513 | 0.2917 | 0.2404 |
| 95% CI (asymptotic) | −0.1384 | 0.1098-0.4736 | 0.0625-0.4183 |
| z-value | 2.6 | | |
| P-value | 0.0081 | | |
| Interpretation | Statistically significant, reject null hypothesis that sample proportions are equal | | |
| n by pi | n * pi <= 5, test inappropriate | | |
| Penetrance Group 2-4 OM score | 77.70% | | |
| Penetrance OM score 1-4 | 77.70% | | |

| | | | |
|---|---|---|---|
| Gene 4 | | COPB2 | |
| Entrez ID | 9276 | | |
| Role | Unknown | Intron Regulatory | |
| Polymorphism | rs7373116 | | |
| Reference | REF | G | |
| Variant | ALT | A | |
| | GG | GA | AA |
| LowMUC | 41.03% | 58.97% | 0.00% |
| HighMuc | 12.50% | 54.17% | 33.33% |
| Predominance | 28.53% | | 33.33% |
| | Sample 1 | Sample 2 | Difference |
| Sample proportion | 0 | 0.3333 | 0.3333 |

| | | | |
|---|---|---|---|
| 95% CI (asymptotic) | 0-0 | 0.1447-0.5219 | 0.164-0.5026 |
| z-value | 3.9 | | |
| P-value | 0.0001 | | |
| Interpretation | Statistically significant, reject null hypothesis that sample proportions are equal | | |
| n by pi | n * pi <= 5, test inappropriate | | |
| Penetrance Group 2-4 OM score | 100% | | |
| Penetrance OM score 1-4 | 100% | | |

| | | | |
|---|---|---|---|
| Gene 5 | | ACTL7B | |
| Entrez ID | 10880 | | |
| Role | Unknown | Intron Regulatory | |
| Polymorphism | rs11787880 | | |
| Reference | REF | A | |
| Variant | ALT | G | |
| | AA | AG | GG |
| LowMUC | 30.77% | 58.97% | 10.26% |
| HighMuc | 4.17% | 50.00% | 45.83% |
| Predominance | 26.60% | | 35.58% |
| | Sample 1 | Sample 2 | Difference |
| Sample proportion | 0.1026 | 0.4583 | 0.3557 |
| 95% CI (asymptotic) | 00074-0.1978 | 0.259-0.6576 | 0.1391-0.5723 |
| z-value | 3.2 | | |
| P-value | 0.0013 | | |
| Interpretation | Statistically significant, reject null hypothesis that sample proportions are equal | | |
| n by pi | n * pi <= 5, test inappropriate | | |
| Penetrance Group 2-4 OM score | 73.30% | | |
| Penetrance OM score 1-4 | 93.30% | | |

| | | | |
|---|---|---|---|
| Gene 6 | | FBX010 | |
| Entrez ID | 26267 | | |
| Role | Unknown | Intron Regulatory | |
| Polymorphism | rs10973387 | | |
| Reference | REF | G | |
| Variant | ALT | A | |
| | GG | GA | AA |
| LowMUC | 35.90% | 56.41% | 7.69% |
| HighMuc | 12.50% | 58.33% | 29.17% |
| Predominance | 23.40% | | 21.47% |
| | Sample 1 | Sample 2 | Difference |
| Sample proportion | 0.769 | 0.2917 | 0.4773 |

| | | | |
|---|---|---|---|
| 95% CI (asymptotic) | 0.6367-0.9013 | 0.1098-0.4736 | 0.2269-0.7277 |
| z-value | 3.7 | | |
| P-value | 0.0002 | | |
| Interpretation | Statistically significant, reject null hypothesis that sample proportions are equal | | |
| n by pi | n * pi > 5, test ok | | |
| Penetrance Group 2-4 OM score | 70% | | |
| Penetrance OM score 1-4 | 100% | | |

| | | | |
|---|---|---|---|
| Gene 7 | SF3B6 | | |
| Entrez ID | 51639 | | |
| Role | Unknown | Minor allele | Synonymous Coding |
| Polymorphism | rs61742149 | | |
| Reference | REF | G | |
| Variant | ALT | A | |
| | GG | GA | |
| LowMUC | 100.00% | 0.00% | |
| HighMuc | 58.33% | 41.67% | |
| Predominance | | 41.67% | |
| | Sample 1 | Sample 2 | Difference |
| Sample proportion | 0 | 0.4167 | 0.4167 |
| 95% CI (asymptotic) | 0-0 | 0.2195-0.6139 | 0.2309-0.6025 |
| z-value | 4.4 | | |
| P-value | <0.0001 | | |
| Interpretation | Statistically significant, reject null hypothesis that sample proportions are equal | | |
| n by pi | n * pi <= 5, test inappropriate | | |
| Penetrance Group 2-4 OM score | 100% | | |
| Penetrance OM score 1-4 | 100% | | |

Note: no AA genotype was present in the 63 patients; the genotype GA is most likely a dominant negative genotype considering that the minor allele A is present less than 5% of the normal population, but 41.67% of patients who were in Group 2-4 OM and none in the Group 0-1.

| | | | |
|---|---|---|---|
| Gene 8 | MRPS22 | | |
| Entrez ID | 56945 | | |
| Role | Unknown | Intron Regulatory | |
| Polymorphism | rs10935321 | | |
| Reference | REF | G | |
| Variant | ALT | A | |
| | GG | GA | AA |
| LowMUC | 41.03% | 58.97% | 0.00% |
| HighMuc | 12.50% | 54.17% | 33.33% |
| Predominance | 28.53% | | 33.33% |
| | Sample 1 | Sample 2 | Difference |
| Sample proportion | 0 | 0.3333 | 0.3333 |
| 95% CI (asymptotic) | 0-0 | 0.1447-0.5219 | 0.164-0.5026 |
| z-value | 3.9 | | |
| P-value | 0.0001 | | |
| Interpretation | Statistically significant, reject null hypothesis that sample proportions are equal | | |
| n by pi | n * pi <= 5, test inappropriate | | |
| Penetrance Group 2-4 OM score | 100% | | |
| Penetrance OM score 1-4 | 100% | | |

| | | | |
|---|---|---|---|
| Gene 9 | FAAH2 | | |
| Entrez ID | 158584 | | |
| Role | Unknown | Intron Regulatory | |
| Polymorphism | | rs4030473 | rs5915052 |
| Reference | REF | T | T |
| Variant | ALT | A | G |
| | TT | TA | AA |
| LowMUC | 76.92% | 12.82% | 10.26% |
| HIghMuc | 45.83% | 16.67% | 33.33% |
| Predominance | 31.09% | | 23.08% |
| | Sample 1 | Sample 2 | Difference |
| Sample proportion | 0.1026 | 0.3333 | 0.2307 |
| 95% CI (asymptotic) | 0.0074-0.1978 | 0.1447-0.5219 | 0.031-0.4304 |
| z-value | 2.3 | | |
| P-value | 0.0235 | | |
| Interpretation | Statistically significant, reject null hypothesis that sample proportions are equal | | |
| n by pi | n * pi <= 5, test inappropriate | | |
| Penetrance Group 2-4 OM score | 67% | | |
| Penetrance OM score 1-4 | 83.30% | | |

| | | | |
|---|---|---|---|
| Gene 10 | MIR54812 | | |
| Entrez ID | 100302277 | | |
| Role | Unknown | microRNA | |
| Polymorphism | | rs111482845 | rs11728441 |
| Reference | REF | TAGAAGG | T |
| Variant | ALT | T | C |
| | TAG | TAG/T | TT |
| LowMUC | 58.97% | 41.03% | 0.00% |
| FlighMuc | 37.50% | 41.67% | 20.83% |
| Predominance | 21.47% | | 20.83% |
| | Sample 1 | Sample 2 | Difference |
| Sample proportion | 0 | 0.2083 | 0.2083 |
| 95% CI (asymptotic) | 0-0 | 0.0458-0.3708 | 0.0709-0.3457 |
| z-value | 3 | | |
| P-value | 0.003 | | |
| Interpretation | Statistically significant, | | |

-continued

| | reject null hypothesis that sample proportions are equal | |
|---|---|---|
| n by pi | n * pi <= 5, test inappropriate | |
| Penetrance Group 2-4 OM score | 100% | |
| Penetrance OM score 1-4 | 100% | |

Example of Non-Significant Gene LIPK:

No significant predominance in Group 2-4 vs. Group 0-1 of the variant allele

No significant z-score

No significant penetrance for any genotype

LIPK had seven SNPs with similar structure as LAMC 1, i.e. altogether homozygote for Ref or Alt alleles or altogether heterozygous (3 combined genotypes possible)

This supports that LAMC1 is a true positive.

| Non-significant gene | | LIPK | | | |
|---|---|---|---|---|---|
| Entrez ID | | 643414 | | | |
| Role | Lipoprotein | | | | |
| Polymorphism | | rs415996 | rs376036 | rs432950 | |
| Reference | REF | C | GA | C | |
| Variant | ALT | T | G | T | |
| Polymorphism | | rs390414 | rs406102 | rs427687 | rs11358016 |
| Reference | REF | A | C | T | A |
| Variant | ALT | T | A | G | G |
| | | CC | CT | TT | |
| LowMUC | | 5.13% | 30.77% | 64.10% | |
| HighMuc | | 8.33% | 62.50% | 29.17% | |
| Predominance | | | | | |
| No increase of the variant homozygous | | | | | |
| No significant increase of the reference | | | | | |
| Assuming that heterozygous CT genotype would represent | | | | | |
| Penetrance Group 2-4 | | 56% | (too low) | | |
| Penetrance OM score 1-4 (CT) | | 70% | (too low) | | |

What is claimed is:

1. A method of treating a subject who has undergone and/or will undergo hematopoietic stem cell transplantation (HSCT) and/or a subject who has undergone and/or will undergo chemotherapy and/or radiation therapy as having an increased risk of developing oral mucositis, comprising:
   a) obtaining a DNA sample from the subject;
   b) contacting the DNA sample from the subject with reagents to determine the presence or absence of each of the following risk alleles:
      1) GG at single nucleotide polymorphism (SNP) site rs4847278;
      2) GG at SNP site rs10797854 and GG at SNP site rs20560 and CC at SNP site rs944970 and CC at SNP site rs1062044 and AA at SNP site rs944971 and GG at SNP site rs6424888 and CC at SNP site rs20563 and CC at SNP site rs2333620;
      3) AA at SNP site rs7373116:
      4) GA at SNP site rs61742149;
      5) AA at SNP site rs10935321; and
      6) TT at SNP site rs111482845 and TT at SNP site rs11728441; and
   c) detecting one or more of: the single risk alleles of (1), (3), (4), or (5) or the multiple risk alleles of (2) or (6) in the DNA sample; and
   thereby identifying the subject as having an increased risk of developing ora mucositis
   d) administering to the subject having one or more of the single, risk alleles or multiple risk alleles in step c) at an increased risk of developing oral mucositis a treatment to optimize Wound healing, a probiotic diet to reduce levels of proinflammatory hydrogen sulfide and/or methylmercaptan produced by oral bacteria, an oral hygiene protocol, amifostine, palifermin, benzidiamine, calcium phosphate, cryotherapy, iseganan, a cryoprotective, a growth factor, topical polyvinylpyrolidone, low power laser irradiation, gene therapy treatment, and any combination thereof.

2. The method of claim 1, further comprising the steps of:
   contacting the DNA sample with reagents to determine the presence of absence of each of the following risk alleles:
      7) GG at SNP site rs147960186;
      8) GG at SNP site rs11787880;
      9) AA at SNP site rs10973387; and
      10) AA at SNP site rs4030473 and GG at SNP site rs5915052; and
   detecting one or more of the single risk alleles of (7), (8) or (9) or the multiple risk alleles of (10) in the DNA sample.

3. The method of claim 1, wherein the cryoprotective is selected from sucralfate, oral glutamine, and hyaluronic acid.

* * * * *

UNITED STATES PATENT AND TRADEMARK OFFICE
CERTIFICATE OF CORRECTION

PATENT NO. : 10,400,271 B1  
APPLICATION NO. : 16/285819  
DATED : September 3, 2019  
INVENTOR(S) : Mougeot et al.

Page 1 of 1

It is certified that error appears in the above-identified patent and that said Letters Patent is hereby corrected as shown below:

In the Claims

Column 27, Line 37, Claim 1: Please correct "ora" to read -- oral --

Column 28, Line 14, Claim 1: Please correct "Wound" to read -- wound --

Column 28, Lines 17-18, Claim 1: Please correct "benzidi-amine," to read -- benzidamine --

Signed and Sealed this  
Twenty-fourth Day of December, 2019

Andrei Iancu  
*Director of the United States Patent and Trademark Office*

SEQUENCE LISTING

<160> NUMBER OF SEQ ID NOS: 6

<210> SEQ ID NO 1
<211> LENGTH: 22
<212> TYPE: DNA
<213> ORGANISM: Homo sapiens

<400> SEQUENCE: 1
tgcatctctt aaatatgtgt ga                                        22

<210> SEQ ID NO 2
<211> LENGTH: 31
<212> TYPE: DNA
<213> ORGANISM: Homo sapiens

<400> SEQUENCE: 2
accacagcca cccttggatc ccccacaaga g                              31

<210> SEQ ID NO 3
<211> LENGTH: 12
<212> TYPE: DNA
<213> ORGANISM: Homo sapiens

<400> SEQUENCE: 3
ggtcactggg ca                                                   12

<210> SEQ ID NO 4
<211> LENGTH: 10
<212> TYPE: DNA
<213> ORGANISM: Homo sapiens

<400> SEQUENCE: 4
acaggtcaat                                                      10

<210> SEQ ID NO 5
<211> LENGTH: 20
<212> TYPE: DNA
<213> ORGANISM: Homo sapiens

<400> SEQUENCE: 5
gttctgggag ctcctccccc                                           20

<210> SEQ ID NO 6

```
<211> LENGTH: 11
<212> TYPE: DNA
<213> ORGANISM: Homo sapiens

<400> SEQUENCE: 6
acgcgcgcgc g                                                            11
```